(12) United States Patent
Hidari

(10) Patent No.: US 11,439,496 B2
(45) Date of Patent: Sep. 13, 2022

(54) TUBULAR THERAPEUTIC IMPLEMENT, TUBULAR THERAPEUTIC IMPLEMENT SET, AND DEVICE FOR INDWELLING TUBULAR THERAPEUTIC IMPLEMENT

(71) Applicant: SB-KAWASUMI LABORATORIES, INC., Kanagawa (JP)

(72) Inventor: Kentaro Hidari, Oita (JP)

(73) Assignee: SB-KAWASUMI LABORATORIES, INC., Kanagawa (JP)

( * ) Notice: Subject to any disclaimer, the term of this patent is extended or adjusted under 35 U.S.C. 154(b) by 0 days.

(21) Appl. No.: 16/647,531

(22) PCT Filed: Oct. 19, 2018

(86) PCT No.: PCT/JP2018/038969
§ 371 (c)(1),
(2) Date: Mar. 16, 2020

(87) PCT Pub. No.: WO2019/078346
PCT Pub. Date: Apr. 25, 2019

(65) Prior Publication Data
US 2020/0214826 A1   Jul. 9, 2020

(30) Foreign Application Priority Data

Oct. 20, 2017  (JP) .............................. JP2017-204028
Oct. 25, 2017  (JP) .............................. JP2017-206517

(51) Int. Cl.
*A61F 2/07* (2013.01)
*A61F 2/954* (2013.01)
(Continued)

(52) U.S. Cl.
CPC ................ *A61F 2/07* (2013.01); *A61F 2/856* (2013.01); *A61F 2/954* (2013.01); *A61F 2002/067* (2013.01); *A61F 2250/0098* (2013.01)

(58) Field of Classification Search
CPC .. A61F 2/07; A61F 2/856; A61F 2/954; A61F 2002/072; A61F 2002/075; A61F 2002/077
See application file for complete search history.

(56) References Cited

U.S. PATENT DOCUMENTS

| 8,870,939 | B2 * | 10/2014 | Roeder ..................... A61F 2/07 623/1.13 |
| 2004/0106980 | A1 * | 6/2004 | Solovay .................... A61F 2/07 623/1.13 |

(Continued)

FOREIGN PATENT DOCUMENTS

| JP | 2003-518982 | 6/2003 |
| JP | 2009-540930 | 11/2009 |

(Continued)

OTHER PUBLICATIONS

International Search Report and the Written Opinion dated Dec. 18, 2018 From the International Searching Authority Re. Application No. PCT/JP2018/038969 and Its Translation of Search Report Into English. (12 Pages).

*Primary Examiner* — William H Matthews

(57) ABSTRACT

Provided are a tubular therapeutic implement, a tubular therapeutic implement set, and a tubular therapeutic implement indwelling device, all of which enable appropriate indwelling at a branching portion in a tubular tissue. This stent graft 30 is provided with: a frame portion (32) having a plurality of frame pieces (321-325); and a tubular graft portion (33) which is provided along the frame portion, wherein the tube wall of the graft portion is provided with (Continued)

a lateral opening (through-hole 36 of a branching section 35) that is connected with an inner cavity of the graft portion, and when the region between one end and the other end of the graft portion is compartmented into a first region (P) that includes the lateral opening and a second region (Q) that dose not include the lateral opening, the frame pieces are not situated in the first region, but are in the second region.

10 Claims, 15 Drawing Sheets

(51) Int. Cl.
*A61F 2/856* (2013.01)
*A61F 2/06* (2013.01)

(56) References Cited

U.S. PATENT DOCUMENTS

| | | | |
|---|---|---|---|
| 2005/0131518 A1* | 6/2005 | Hartley | A61F 2/856 623/1.13 |
| 2011/0313512 A1 | 12/2011 | Hartley et al. | |
| 2017/0049588 A1 | 2/2017 | Davis et al. | |

FOREIGN PATENT DOCUMENTS

| | | |
|---|---|---|
| JP | 2012-525227 | 10/2012 |
| JP | 5789867 | 8/2015 |
| JP | 2018-051259 | 4/2018 |
| JP | 2018-051259 | 8/2020 |
| WO | WO 2019/078346 | 4/2019 |

* cited by examiner

TUBULAR THERAPEUTIC IMPLEMENT, TUBULAR THERAPEUTIC IMPLEMENT SET, AND DEVICE FOR INDWELLING TUBULAR THERAPEUTIC IMPLEMENT

TECHNICAL FIELD

The present invention relates to a tubular therapeutic implement, a tubular therapeutic implement set, and a tubular therapeutic implement indwelling device.

BACKGROUND ART

Conventionally, there have been known branching blood vessel-compatible stent grafts as stent grafts used for treating aortic aneurysm, aortic dissection, or the like caused in aorta (e.g. see Patent Documents 1 and 2). The conventional stent grafts described in Patent Documents 1 and 2 have a frame portion which is a so-called stent, and a graft portion fixed to the frame portion. A branching portion having a side opening communicating with an inner cavity of the graft portion is disposed on a tube wall of the graft portion. In the conventional stent graft, while the conventional stent graft is situated in a main blood vessel, a branching blood vessel stent graft is joined to the branching portion, and the branching blood vessel stent graft is situated in a branching blood vessel, so that bloodstreams in the main blood vessel and the branching blood vessel are maintained.

PRIOR ART DOCUMENT

Patent Document

Patent Document 1: Japanese Patent Publication No. 5789867
Patent Document 2: Japanese Unexamined Patent Application Publication No. 2009-540930

SUMMARY OF THE INVENTION

Technical Problem

At a practice site where stent graft indwelling is performed, it has been requested to indwell a stent graft with a high positional accuracy for minimizing displacement between a blood vessel opening of a branching blood vessel and a side opening of the stent graft. Such a request may occur also for a tubular therapeutic implement intended to be indwelled in a tubular tissue other than blood vessel (e.g. a digestive tract, bile duct, or the like).

In addition, when a branching blood vessel stent graft is attached to the branching portion of the stent graft in a conventional stent graft, a through-hole (side opening) of the branching portion is not sufficiently opened and is deformed in some cases. If the through-hole on the branching portion is not properly opened, an opening edge of the branching portion does not sufficiently come into close contact with the branching blood vessel stent graft, and blood may leak out from a gap generated on a joint part. Such a problem can also be caused in an indwelling tubular therapeutic implement other than stent grafts, e.g. an artificial blood vessel having no stent frame.

An object of the present invention is to provide a tubular therapeutic implement, a tubular therapeutic implement set, and a tubular therapeutic implement indwelling device, which can be appropriately indwelled in a branching part of a tubular tissue.

Solution to Problem

The tubular therapeutic implement according to the present invention includes a frame portion having a plurality of frame pieces, and a graft portion in a tubular shape disposed along the frame portion, in which a tube wall of the graft portion has a side opening communicating with an inner cavity of the graft portion, and when a region from one end to the other end of the graft portion is demarcated into a first region including the side opening and a second region that does not include the side opening, the frame pieces are situated not in the first region but in the second region.

The tubular therapeutic implement set according to the present invention includes a first tubular therapeutic implement, and a second tubular therapeutic implement having openings on both ends, in which the first tubular therapeutic implement is the aforementioned tubular therapeutic implement, and the second tubular therapeutic implement is configured to be attachable to the side opening of the first tubular therapeutic implement.

The tubular therapeutic implement indwelling device according to the present invention is intended to indwell a tubular therapeutic implement expandable in a radial direction, in which the tubular therapeutic implement is the aforementioned tubular therapeutic implement.

Advantageous Effect of the Invention

According to the present invention, a tubular therapeutic implement can be appropriately indwelled on a branching part of a tubular tissue.

DESCRIPTION OF THE EMBODIMENT

Hereinafter, the tubular therapeutic implement, the tubular therapeutic implement set, and the tubular therapeutic implement indwelling device according to the present invention will be explained on the basis of the embodiments illustrated in the figures.

First Embodiment

In the first embodiment, a case that the tubular therapeutic implement, the tubular therapeutic implement set, and the tubular therapeutic implement indwelling device according to the present invention are applied to a stent graft 30, a stent graft set 5, and a stent graft-indwelling device 1 respectively will be explained as an example.

Figure 1A:
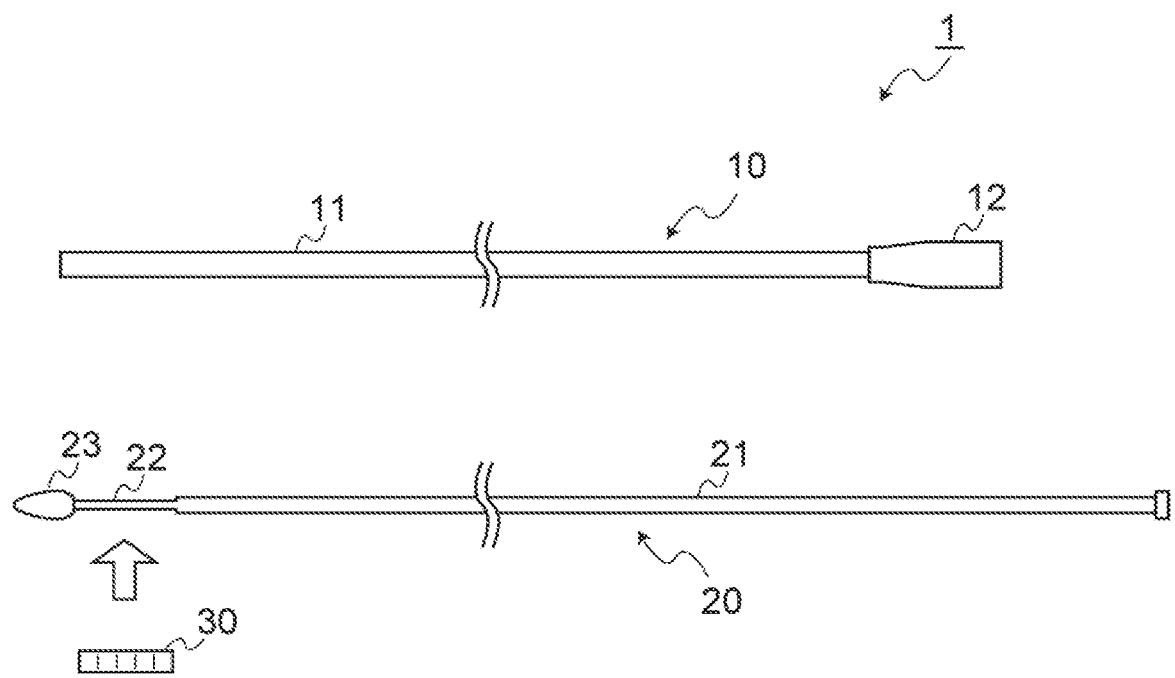
FIG. 1A is a drawing illustrating respective members constituting a stent graft-indwelling device according to an embodiment.
Figure 1B:
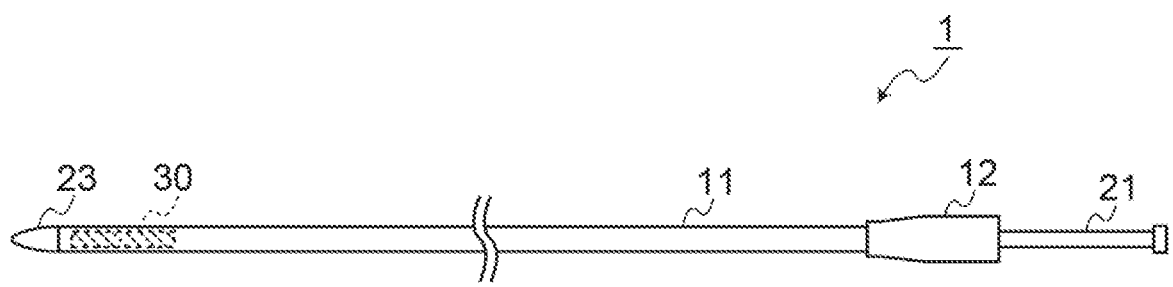
FIG. 1B is a drawing illustrating a state that the respective members are assembled.

First, a configuration of the stent graft-indwelling device 1 according to the first embodiment will be explained with reference to FIG. 1A and FIG. 1B. In FIG. 1A and FIG. 1B, a size (length, diameter, or the like), a shape, and the like of each member constituting the stent graft-indwelling device 1 are schematically illustrated for facilitating comprehension of the present invention. Additionally, in FIG. 1A and FIG. 1B, the right side of the figure is referred to as a proximal end side, and the left side of the figure is referred to as a distal end side.

As illustrated in FIG. 1A and FIG. 1B, the stent graft-indwelling device 1 (tubular therapeutic implement indwelling device) includes a tubular sheath 10, an inner rod 20, and the stent graft 30. The inner rod 20 is situated inside the sheath 10 and is configured to be able to advance and retreat in the sheath 10 along the axial direction (longitudinal direction) of the sheath 10. The stent graft-indwelling device 1 is an indwelling device used for indwelling a stent graft e.g. in a blood vessel of a thoracic aorta.

The sheath 10 has a tubular sheath main body portion 11, and a hub 12 disposed on the proximal end side of the sheath main body portion 11. Although not illustrated in the figure, the hub 12 has a nut for fixing the inner rod 20 to the sheath 10 or releasing the fixation.

The sheath 10 is made of a flexible material. Examples of the flexible material include: a biocompatible synthetic resin (elastomer) selected from a fluororesin, a polyamide-based resin, a polyethylene-based resin, and a polyvinyl chloride-based resin, and the like; a resin compound obtained by blending other materials into these resins; a multi-layered structure made of these synthetic resins; and a complex of these synthetic resins and a metal wire.

The inner rod 20 has a bar-like rod portion 21, a holding portion 22 for holding the contracted stent graft 30, and a distal end tip 23 disposed on the distal end portion of the inner rod 20. A diameter of the holding portion 22 is set to be smaller than that of the rod portion 21 e.g. by only a thickness of the stent graft 30.

Examples of materials constituting the rod main body portion 21 and the holding portion 22 include various materials having appropriate hardness and flexibility, such as a resin (plastic, elastomer) or a metal. Examples of a material constituting the distal end tip 23 include various materials having appropriate hardness and flexibility, such as a synthetic resin (elastomer) selected from e.g. a polyamide-based resin, a polyurethane-based resin, and a polyvinyl chloride-based resin.

Although not illustrated in the figure, on the rod main body portion 21, the holding portion 22, and the distal end tip 23, e.g. a guide wire lumen through which a guide wire is inserted, a trigger wire lumen through which a trigger wire for expanding the contracted stent graft 30 at a lesion is inserted, or the like is formed along an axial direction (longitudinal direction) of the inner rod 20.

Next, a configuration of the stent graft 30 according to the embodiment will be explained with reference to FIG. 2A to FIG. 2C. In each of these figures, a thickness, a width, and the like of a graft portion 33 and a branching portion 35 of the stent graft 30 are exaggeratedly illustrated for facilitating comprehension of the present invention.

Figure 2A:
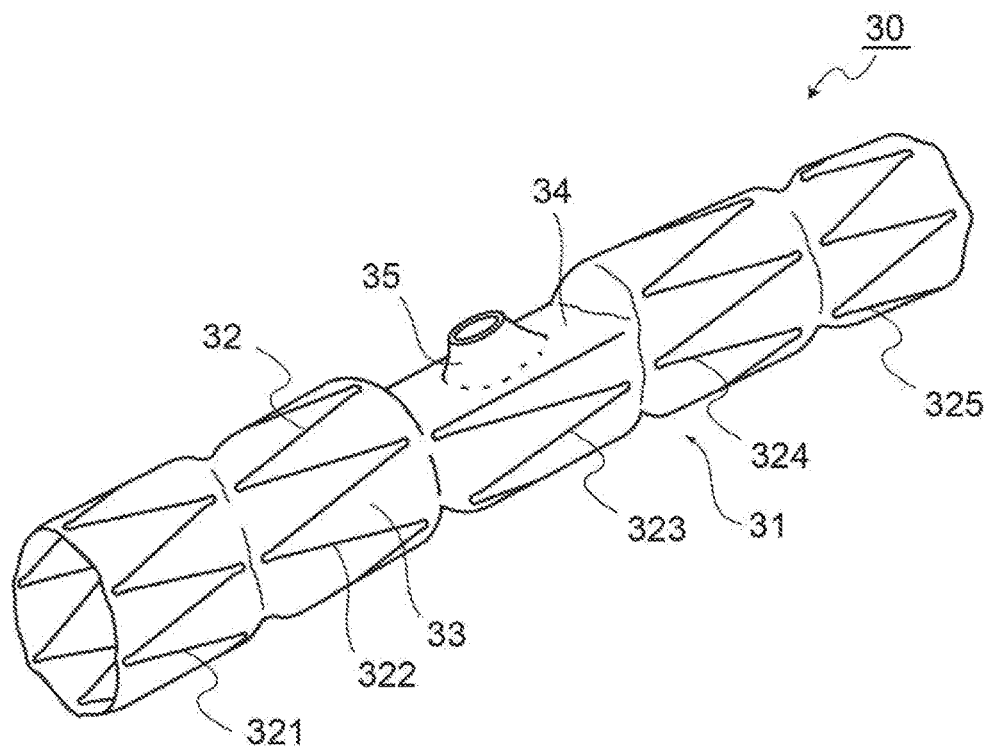
FIG. 2A is an external perspective drawing of the stent graft according to the embodiment.
Figure 2B:
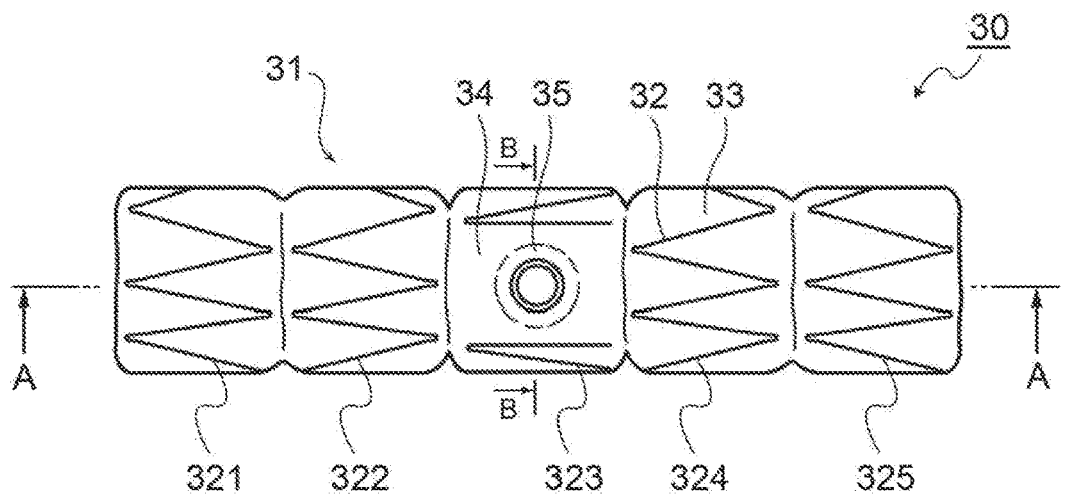
FIG. 2B is a plan drawing of the stent graft.
Figure 2C:
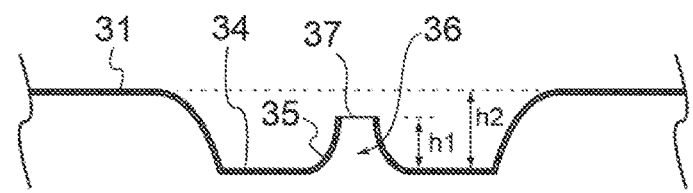
FIG. 2C is a cross-sectional drawing taken along Line A-A in FIG. 2B, and is an enlarged drawing of a peripheral part of a branching portion.

As illustrated in FIG. 2A and FIG. 2B, the stent graft 30 includes a tubular main body portion 31 having openings on both ends, and the branching portion 35 disposed on a tube wall of the main body portion 31. The main body portion 31 includes a tubular frame portion 32, and the graft portion in the tubular shape 33 disposed along the frame portion 32. The branching portion 35 is disposed on a tube wall of the graft portion 33 and has a through-hole 36 (side opening) communicating with an inner cavity of the graft portion 33.

In this embodiment, although a case of the straight pipe-shaped stent graft 30 is described as an example, the present invention is not limited to this case. The stent graft 30 may be an arched shape or a twistedly bent shape.

The frame portion 32 is a self-expandable stent frame formed into a tube, and includes five frame pieces 321 to 325 having a thin metal wire folded in a zigzag pattern. The frame portion 32 is configured to be able to deform from a state of contracting inward in a radial direction to a state of expanding outward in the radial direction and defining a tubular flow path. Examples of a material constituting the frame portion 32 (frame pieces 321 to 325) include known metals or metal alloys represented by a stainless steel, a Ni—Ti alloy, a titanium alloy, and the like.

The graft portion 33 is fixed to the frame portion 32 so as to cover the frame portion 32 along the frame portion 32, and defines the aforementioned tubular flow path. The graft portion 33 may cover the frame portion 32 from an outer periphery or an inner periphery, or so as to sandwich the frame portion 32 from both the outer and inner peripheries of the frame portion 32. Examples of a material of the graft portion 33 include a fluororesin such as PTFE (polytetrafluoroethylene), and a polyester resin such as polyethylene terephthalate.

As illustrated in FIG. 2A, a concave portion 34 where the outer peripheral face is partially recessed inward in a radial direction is formed on a part of the graft portion 33 (middle position of the graft portion 33). The concave portion 34 has a flat bottom face, and the branching portion 35 is situated at a center position of the bottom face.

The branching portion 35 has a cylindrical shape protruding outward in a radial direction of the graft portion 33 from the tube wall of the graft portion 33 (bottom face of the concave portion 34). As illustrated in FIG. 2C, under a condition that a protrusion height of the branching portion 35 is defined as h1 and a depth of the concave portion 34 is defined as h2, a relationship "h1<h2" is satisfied. In addition, the branching portion 35 is made of the same material as of the graft portion 33, and is formed integrally with the graft portion 33. Thereby, the branching portion 35 has such a flexibility that an opening direction can be changed by e.g. a bloodstream from a main blood vessel to a branching blood vessel.

In the stent graft 30 according to the first embodiment, when a region from one end to the other end of the graft portion 33 is demarcated into a "first region P" including the through-hole 36 (side opening) of the branching portion 35 and a "second region Q" does not include the through-hole 36 (side opening) of the branching portion 35, the frame pieces 321 to 325 constituting the frame portion 32 are situated not on the first region P but on the second region Q. This arrangement will be explained in detail below with reference to FIG. 2 and FIG. 3. For facilitating comprehension of the present invention, the first region P is indicated with a thick line in FIG. 3B, and the second region Q is indicated with a thick line in FIG. 3C.

First, when the graft portion 33 is demarcated into each section of the five frame pieces 321 to 325, the region having the frame piece 321 does not include the branching portion 35, with reference to FIG. 2A and FIG. 2B. That means, the region having the frame piece 321 corresponds to the "second region Q" according to the aforementioned demarcation. Similarly, the regions having the frame pieces 322, 324, and 325 correspond to the "second region Q" due to lack of the branching portion 35.

Figure 3A:
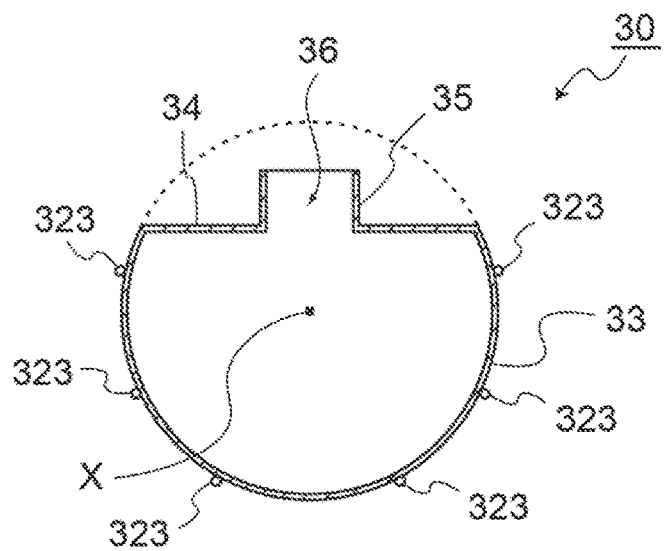
FIG. 3A is a cross-sectional drawing taken along Line B-B in FIG. 2B, and is an enlarged cross-sectional drawing illustrating a state that the stent graft is cut at a position of a through-hole.

In the region having the frame piece 323, the region having the concave portion 34 has a branching portion 35 as illustrated in FIG. 3A. That means, the region having the concave portion 34 is a region including the through-hole 36 (side opening) of the branching portion 35, and corresponds to the "first region P". On the other hand, in the tube wall in FIG. 3A, the region having the frame piece 323 corresponds to the "second region Q". That means, when a peripheral face of the graft portion 33 is demarcated into the "first region P" does not have the frame pieces 321 to 325 constituting the frame portion 32 and the "second region Q" having the frame pieces 321 to 325, the through-hole 36 (side opening) of the branching portion 35 is situated in the first region P.

Figure 3B:
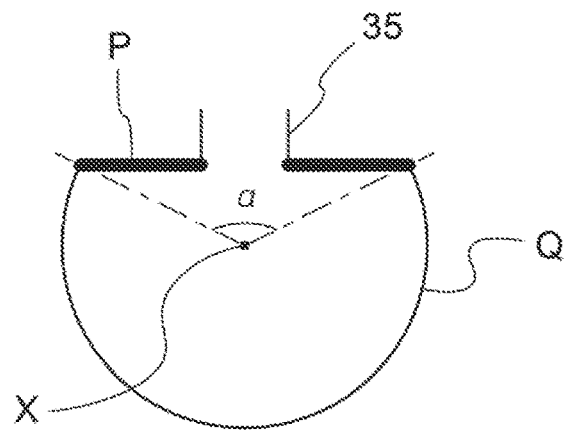
FIG. 3B is a schematic drawing illustrating a position of a first region in the cross-section of the stent graft in FIG. 3A.
Figure 3C:
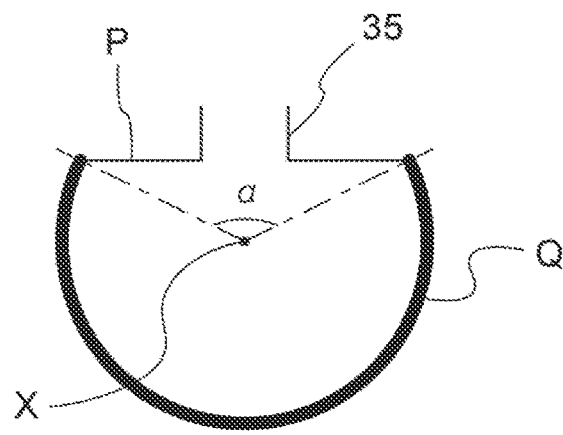
FIG. 3C is a schematic drawing illustrating a position of a second region in the cross-section of the stent graft in FIG. 3A.

An angle α illustrated in FIG. 3B and FIG. 3C is an angle formed by two virtual lines connecting a tube axis X of the graft portion 33 with an edge of the concave portion 34. The angle α is preferably within a range of 90° or more to 180° or less out of the full 360° circumference of the circular cross-section of the graft portion 33, and is set to e.g. 120°.

Next, the configuration of the stent graft set 5 according to the first embodiment will be explained with reference to FIG. 4 and FIG. 5.

Figure 4:
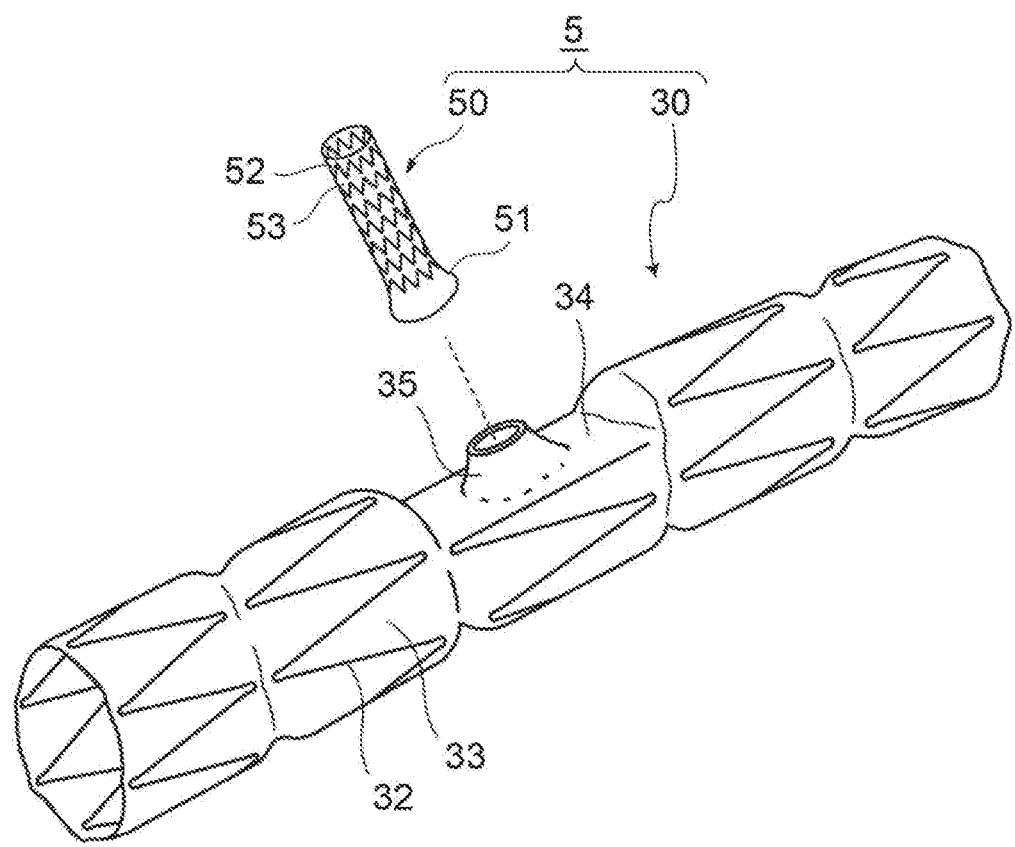
FIG. 4 is an external perspective drawing of a stent graft set according to an embodiment.

As illustrated in FIG. 4, the stent graft set 5 (tubular therapeutic implement set) is obtained by combining the stent graft 30 (first tubular therapeutic implement) with a branching blood vessel stent graft 50 (second tubular therapeutic implement). The configuration of the stent graft 30 is as explained above.

The stent graft 50 is a tubular member having openings on both ends, and defines a tubular flow path through which the bloodstream can pass similarly to the aforementioned stent graft 30. End portion 51 of the stent graft 50 has a flared shape such that the opening area increases towards the opening end. The stent graft 50 has e.g. a frame portion 52 made of a thin metal wire, and a graft portion 53 fixed to the frame portion 52. Since configurations of the frame portion 52 and the graft portion 53 are the same as of the aforementioned frame portion 32 and graft portion 33 of the stent graft 30, detailed explanation of these configurations is omitted.

Figure 5A:
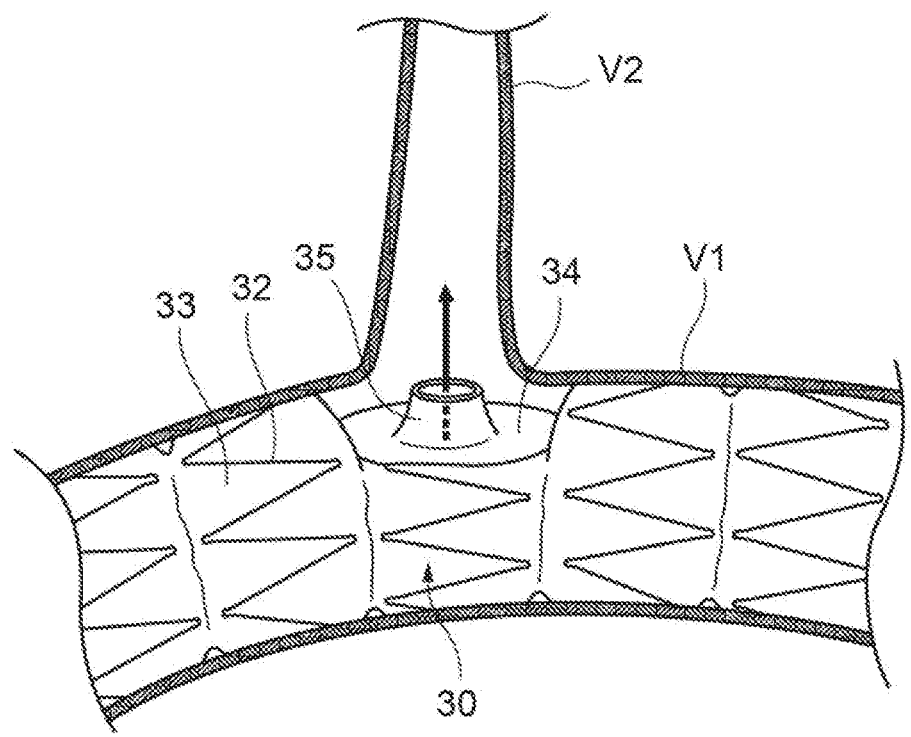
FIG. 5A is a schematic drawing illustrating a state that the stent graft is developed in a blood vessel.
Figure 5B:
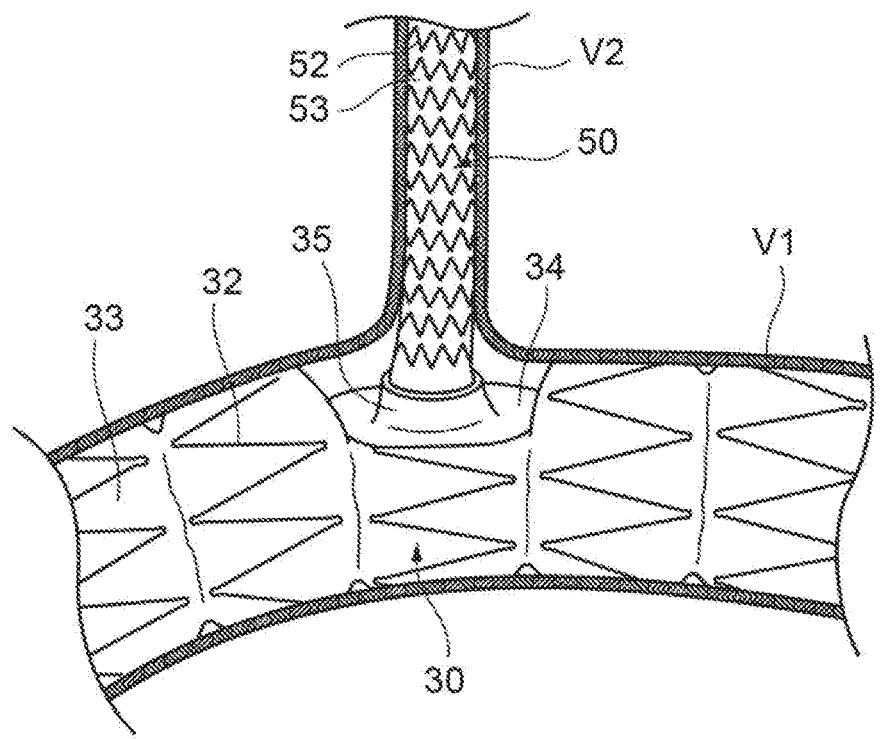
FIG. 5B is a schematic drawing illustrating a state that a branching blood vessel stent graft is attached to the branching portion of the stent graft.

The stent graft 50 is a branching blood vessel stent graft, and is configured to have a diameter smaller than of the aforementioned stent graft 30. When the stent graft 50 is attached to the branching portion 35 of the stent graft 30, the stent graft 30 is already in an expanded state in a main blood vessel V1 as illustrated in FIG. 5A. In this example, the contracted stent graft 50 is inserted from the inside the stent graft 30 such that it is positioned inside of the branching portion 35, and then the stent graft 50 is expanded. At this time, although not illustrated in the figure, the stent graft 50 is indwelled such that an inner face of the through-hole 36 on the branching portion 35 of the stent graft 30 is brought into contact with an outer face of the one end portion 51 of the stent graft 50.

According to the stent graft 30 according to the first embodiment configured as described above, when the stent graft 30 is indwelled at a branching position between the main blood vessel V1 and a branching blood vessel V2, even if the branching portion 35 does not sufficiently coincide with the branching blood vessel V2, the direction and the position of the branching portion 35 can be adjusted to some extent. This is because the frame pieces are not situated in the first region P including the through-hole 36 (side opening) of the branching portion 35 (see FIG. 3B and FIG. 3C) as described above. Thus, the stent graft 30 according to the first embodiment can be indwelled in the branching blood vessel V2 with a positional accuracy higher than before, and therefore can be appropriately indwelled on the branching part of the main blood vessel V1 (tubular tissue).

In the stent graft 30 according to the first embodiment, the first region P is present within a range of 90° or more to 180° or less out of the full 360° circumference of the circular cross-section of the graft portion 33, and the second region Q is present in a range excluding the first region P, as illustrated in FIG. 3B and FIG. 3C. Thereby, the stent graft can be indwelled with a positional accuracy higher than before while maintaining an appropriate strength by the frame piece 323 situated in the second region Q.

Since the stent graft set 5 and the stent graft-indwelling device 1 according to the first embodiment include the aforementioned excellent stent graft 30, the stent graft can be indwelled with a positional accuracy higher than before.

Note that the present invention is not limited to the examples described in the aforementioned first embodiment, and can be implemented in various aspects without departing from the gist of the present invention. For example, the following modifications are also possible.

Figure 6A:
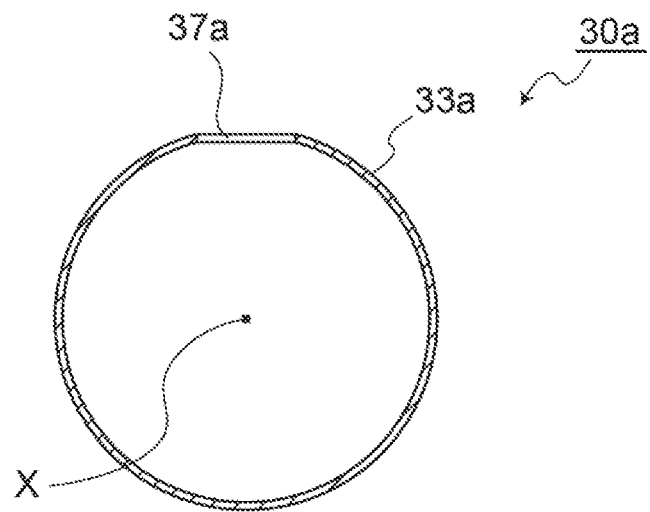
FIG. 6A is an enlarged cross-sectional drawing of a stent graft according to a first embodiment cut at a position of a through-hole, which is a first modification example of the stent graft.
Figure 6B:
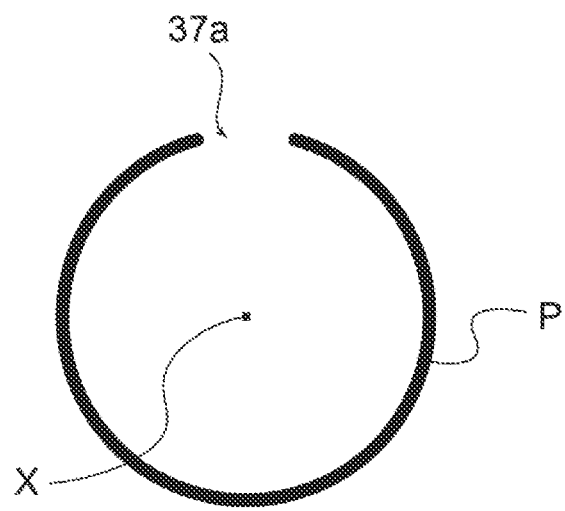
FIG. 6B is a schematic drawing illustrating a position of a first region in the cross-section of the stent graft in FIG. 6A.

For example, a stent graft 30*a* illustrated in FIG. 6A and FIG. 6B has no concave portion on a tube wall of a graft portion 33*a*, and when the graft portion 33*a* is cross-sectioned at a position having an opening 37*a* (side opening), the graft portion 33*a* does not have the frame piece. That means, the first region P is present over the entire circumference of the graft portion 33*a*. Also in this case, a direction and a position of a branching portion 35*a* can be adjusted to some extent, and therefore the stent graft can be indwelled with a positional accuracy higher than before.

Figure 7A:
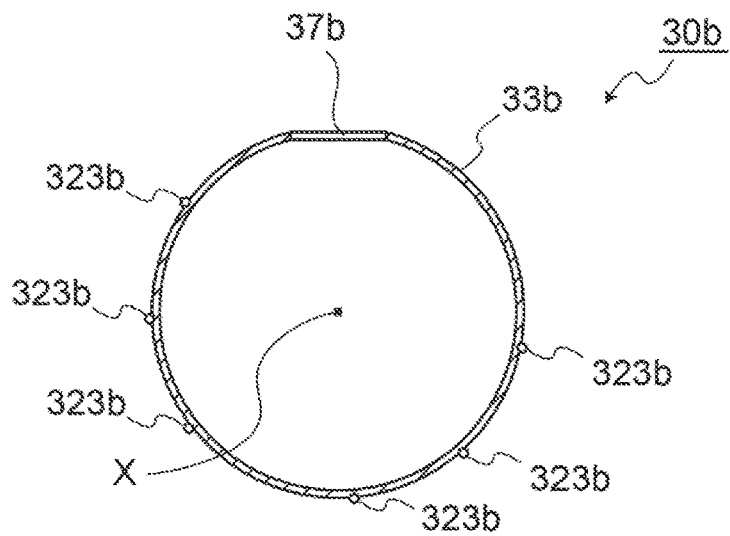
FIG. 7A is an enlarged cross-sectional drawing of the stent graft according to the first embodiment cut at the position of the through-hole, which is a second modification example of the stent graft.
Figure 7B:
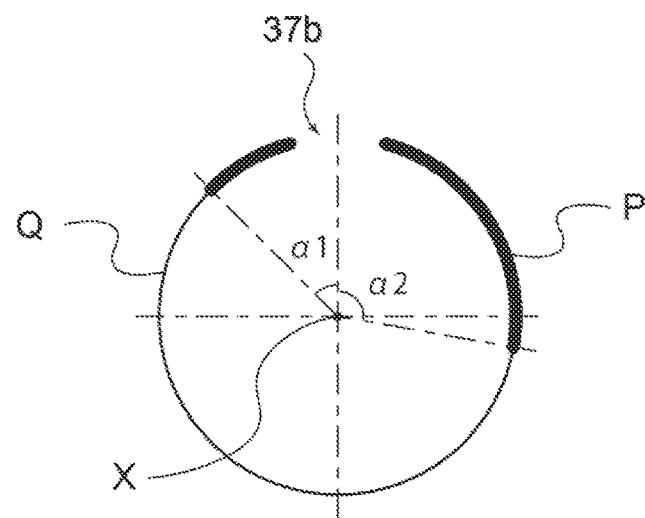
FIG. 7B is a schematic drawing illustrating the position of the first region in the cross-section of the stent graft in FIG. 7A.
Figure 7C:
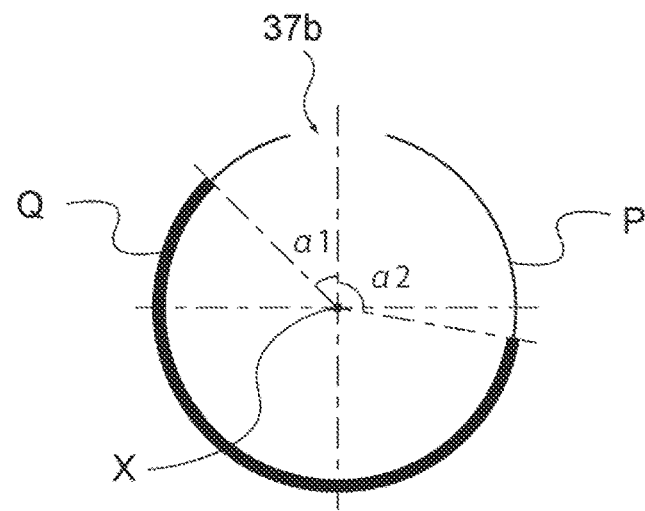
FIG. 7C is a schematic drawing illustrating the position of the second region in the cross-section of the stent graft in FIG. 7A.

In addition, a stent graft 30*b* illustrated in FIG. 7A to FIG. 7C has no concave portion on a tube wall of a graft portion 33*b*, and when the graft portion 33*a* is cross-sectioned at a position having an opening 37*b* (side opening), the position of the first region P deviates from the first region P (see FIG. 3A) of the stent graft 30 described in the first embodiment. Specifically, under a condition that a virtual line connecting a tube axis X of the graft portion 33*b* with an opening center of the opening 37*b* is defined as a reference line, an angle α1 formed by the reference line and a virtual line connecting the tube axis X with a figure's left side edge of the first region P is set to be within a range of 30° to 60° (e.g. 45°), and an angle α2 formed by the reference line and a virtual line connecting the tube axis X with a figure's right side edge of the first region P at the right side of the figure is set to be within a range of 80° to 120° (e.g. 100°). When viewing a position of the opening 37*b* with respect to the first region P, the opening 37*b* substantially deviates from a middle position of the first region P. For example, when a stent graft is indwelled in an arch aorta (aortic arch), even if a branching blood vessel branches from a position of an arch aorta inclined from a greater curvature toward to a back, the stent graft 30*b* of this modification example can be flexibly adapted to the branching blood vessel of the arch aorta by such a way that the angle α1 side is indwelled on the breast side and the angle α2 side is indwelled on the back side. Also in this case, the stent graft can be indwelled with a positional accuracy higher than before while maintaining an appropriate strength by frame pieces situated in the second region Q.

Figure 8:
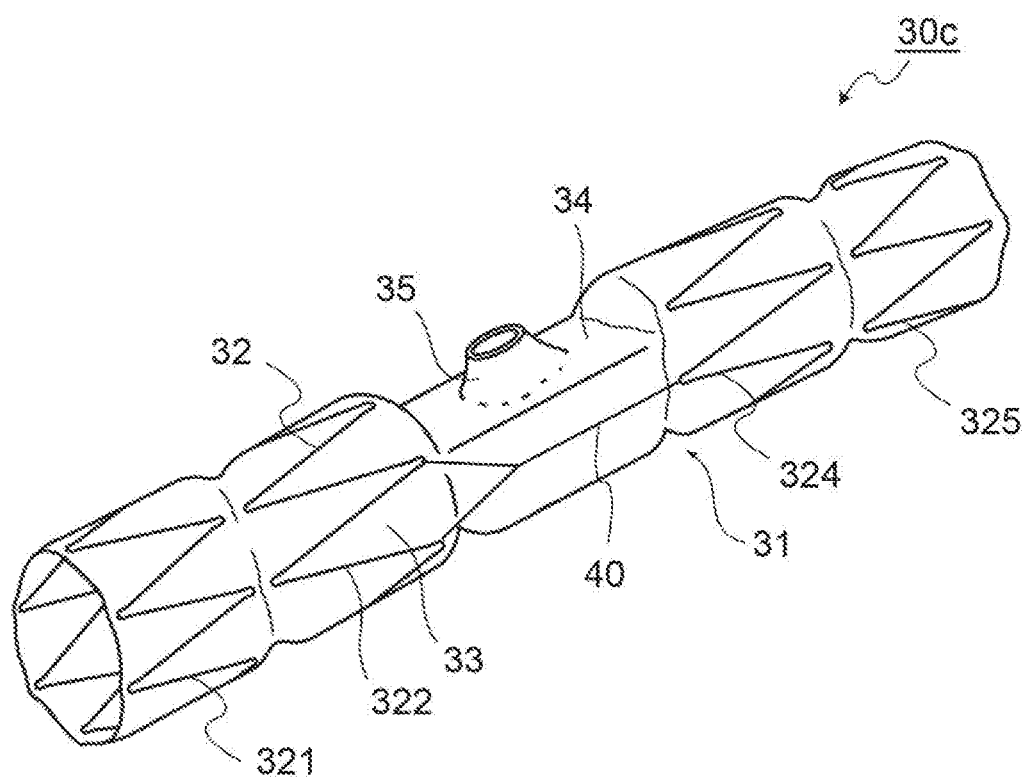
FIG. 8 is an external perspective drawing of the stent graft according to the first embodiment, which is a third modification example of the stent graft.
Figure 9A:
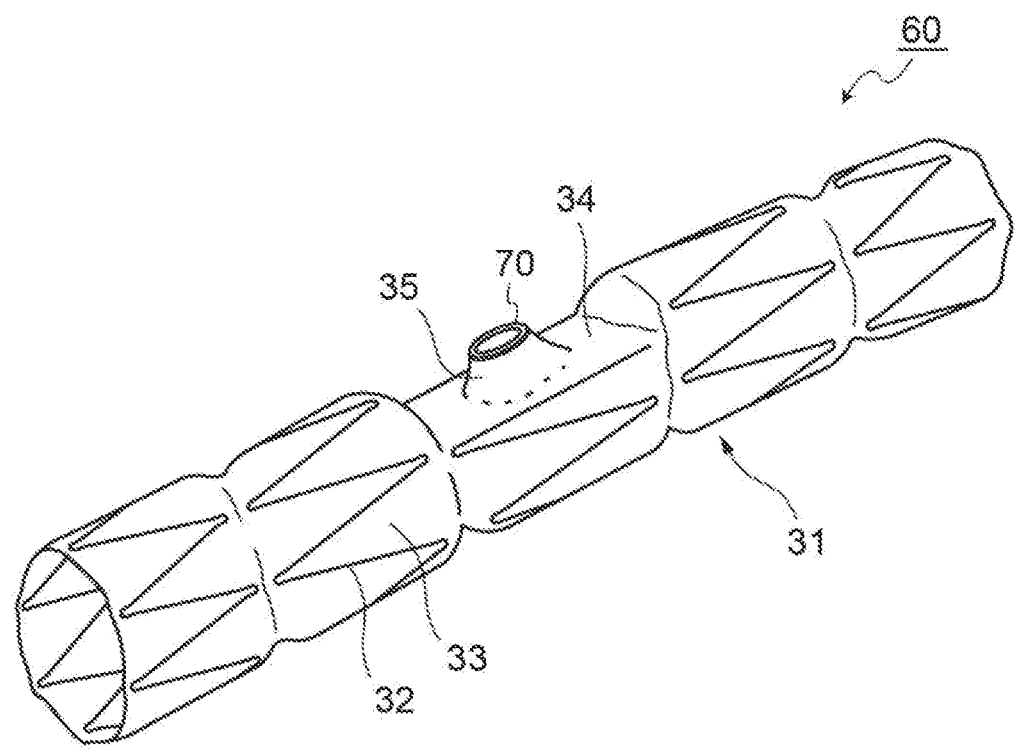
FIG. 9A is an external perspective drawing of a stent graft according to a second embodiment.
Figure 9B:
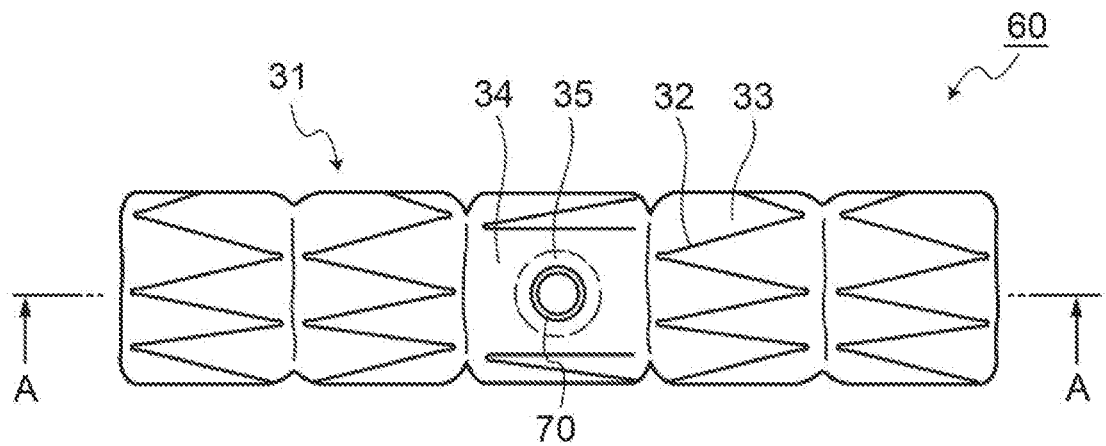
FIG. 9B is a plan drawing of the stent graft.
Figure 9C:
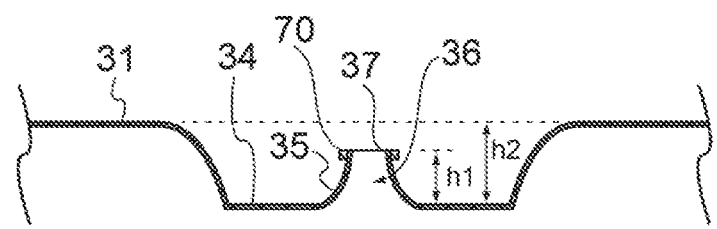
FIG. 9C is a cross-sectional drawing taken along Line A-A in FIG. 9B, and is an enlarged drawing of a peripheral part of a branching portion.

Additionally, in a stent graft 30*c* illustrated in FIG. 8, a connecting member 40 connected to the frame pieces 322 and 324 is situated instead of the frame piece (frame piece 323 illustrated in FIG. 2A) situated in the region of the branching portion 35 among five frame pieces. Incidentally, a shape of the connecting member 40 illustrated in FIG. 8 is a Y-shape, but is not limited to this shape. The shape of the connecting member 40 may be a linear shape, or a curved shape such as an S-shape. In addition, the connecting member 40 can be made of the same material as that of the frame pieces, but may be made of a different material from that of the frame piece. As a method of connecting between the connecting member 40 and the frame pieces 322 and 324, various joining methods such as caulking joining using a connecting pipe, welding, and adhesion can be adopted.

Furthermore, an annular member 70 according to the second embodiment can also be applied to the stent graft 30. That means, the branching portion 35 of the stent graft 30 may have the annular member 70 (opening state-maintaining portion) which maintains the opening state of the through-hole 36 (side opening) on the branching portion 35 when the graft portion 33 is expanded. The annular member 70 as the opening state-maintaining portion will be described in detail in the second embodiment.

Second Embodiment

In the second embodiment, a case that the tubular therapeutic implement, the tubular therapeutic implement set, and the tubular therapeutic implement indwelling device according to the present invention are applied to a stent graft 60, a stent graft set 6, and the stent graft-indwelling device 1 respectively will be explained as an example.

A configuration of the stent graft 60 according to the second embodiment is different from the stent graft 30 according to the first embodiment in that the stent graft 60 has the annular member 70 in a vicinity of an opening edge 38 on the through-hole 36 (side opening) of the branching portion 35. As for the stent graft 60, the same constituents as in the stent graft 30 according to the first embodiment are given the same reference symbols, and explanation of the constituents will be omitted. In addition, like the stent graft 30 according to the first embodiment, the stent graft 60 according to the second embodiment can be indwelled e.g. in a blood vessel of a thoracic aorta by using the stent graft-indwelling device 1 (see FIG. 1).

In the stent graft 60, the material constituting the frame portion 32 is not situated on the branching portion 35. Excluding the annular member 70 described later, the branching portion 35 is made of the same material as of the graft portion 33 of the main body portion 31, and is formed integrally with the graft portion 33. Thereby, the branching portion 35 has such a flexibility that an opening direction can be changed by e.g. a bloodstream from a main blood vessel to a branching blood vessel.

As illustrated in FIG. 9A to FIG. 9C and FIG. 10B, the annular member 70 as the opening state-maintaining portion is situated on the outer peripheral face of the through-hole 36 in the branching portion 35. The branching portion 35 and the annular member 70 are connected to each other e.g. by heat welding. Alternatively, the branching portion 35 and the annular member 70 may be connected to each other using a method other than the heat welding (e.g. ultrasonic welding, pressure bonding, adhesion, sewing, or the like).

Figure 10A:
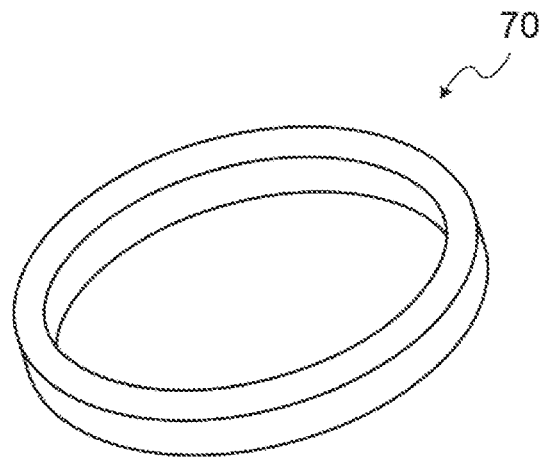
FIG. 10A is an enlarged external perspective drawing of an annular member.
Figure 10B:
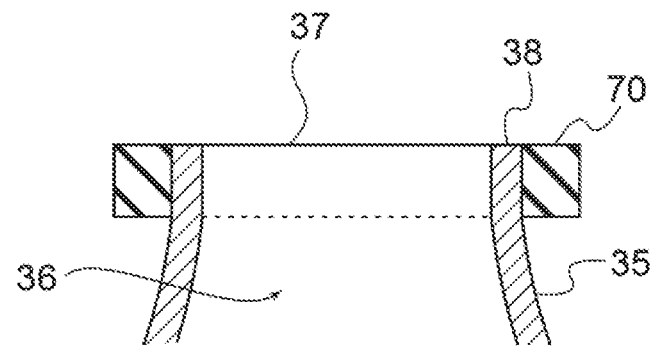
FIG. 10B is an enlarged cross-sectional drawing of a vicinity of the annular member in FIG. 9C.

As illustrated in FIG. 10A and FIG. 10B, the annular member 70 is e.g. a circle (ring-shaped) member having a square cross-section. The annular member 70 is made of a high elasticity material, e.g. a silicone rubber.

The annular member 70 has a function of maintaining the opening state of the through-hole 36 when the main body portion 31 is expanded. In other words, the annular member 70 has a function of maintaining the opening dimension of the through-hole 36 larger than a predetermined dimension so as to prevent the opening edge 38 of the branching portion 35 from closing while the main body portion 31 is expanded.

Next, a configuration of the stent graft set 6 according to the second embodiment will be explained with reference to FIG. 11 to FIG. 13. For facilitating comprehension of the present invention, in FIG. 13 a thickness and a width of each member are exaggeratedly illustrated.

Figure 11:
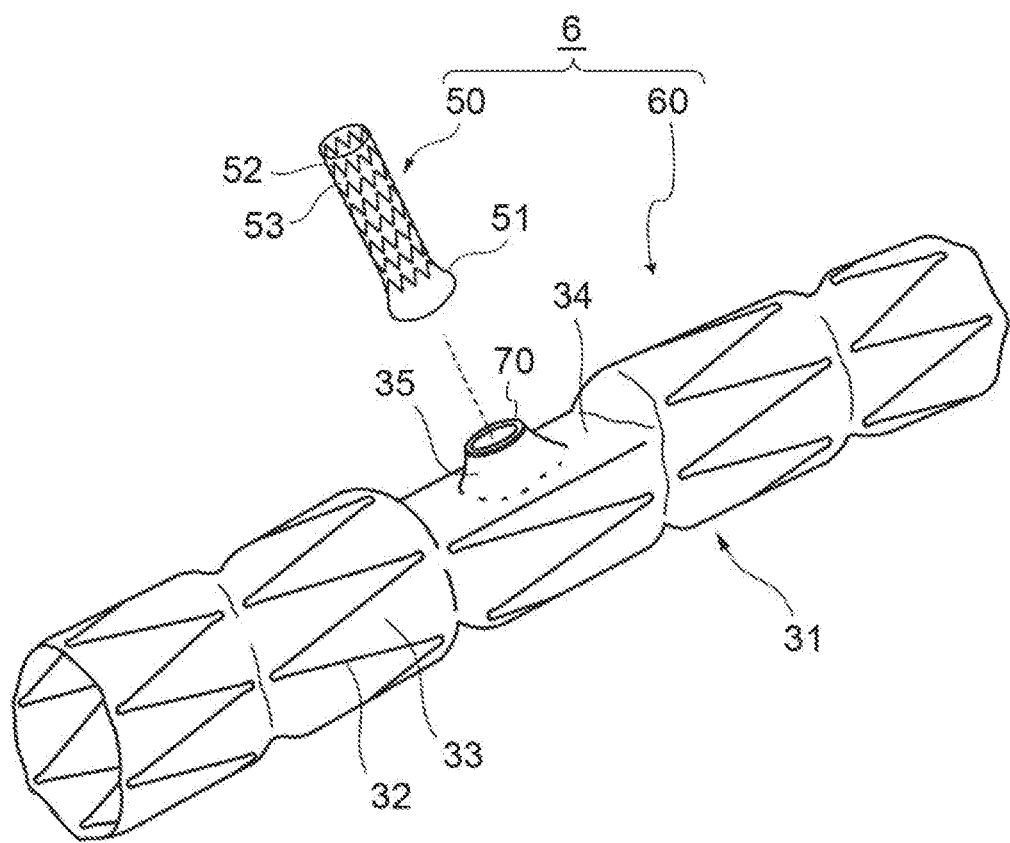
FIG. 11 is an external perspective drawing of a stent graft set according to the second embodiment.

As illustrated in FIG. 11, the stent graft set 6 (tubular therapeutic implement set) is obtained by combining the stent graft 60 (first tubular therapeutic implement) with a branching blood vessel stent graft 50 (second tubular therapeutic implement). The configuration of the stent graft 60 is as explained above. Also, the configuration of the stent graft 50 is as explained in the first embodiment.

Figure 12A:
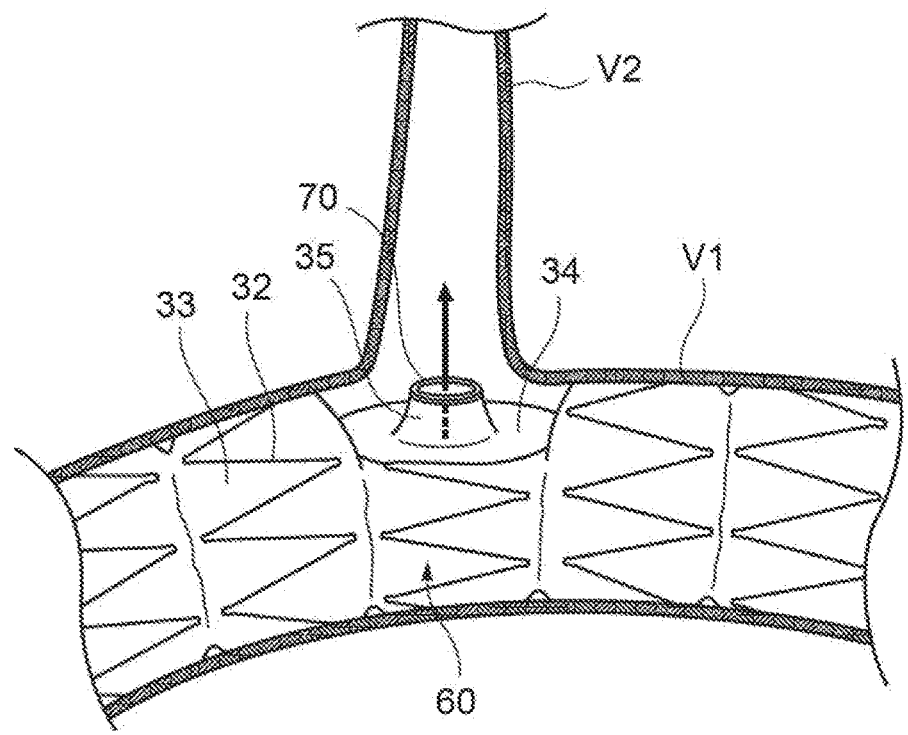
FIG. 12A is a schematic drawing illustrating a state that the stent graft is developed in a blood vessel.
Figure 12B:
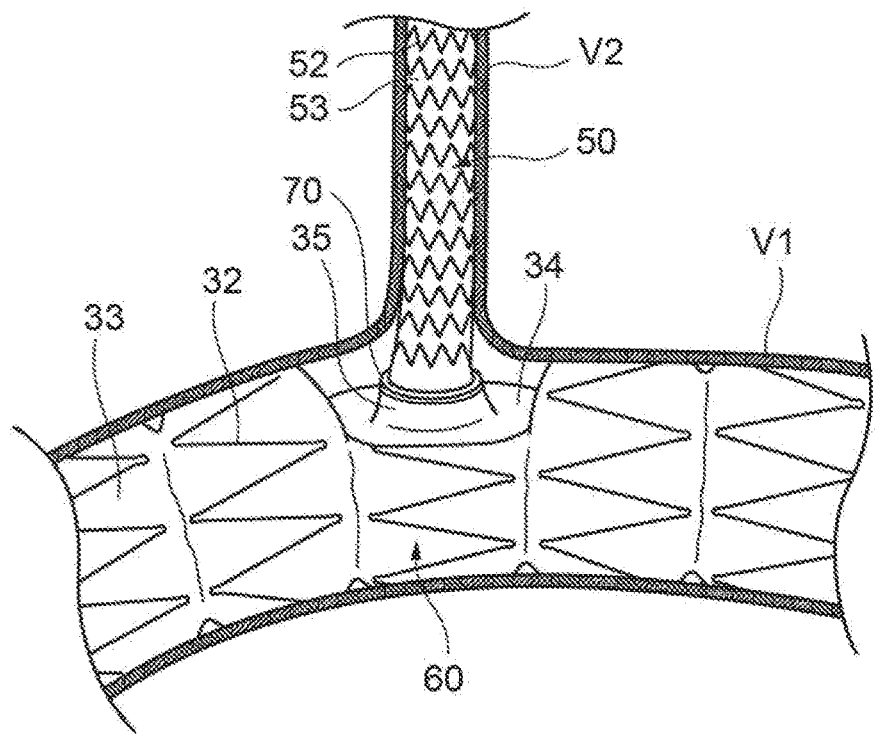
FIG. 12B is a schematic drawing illustrating a state that a branching blood vessel stent graft is attached to the branching portion of the stent graft.

When the branching blood vessel stent graft 50 is attached to the branching portion 35 of the stent graft 60, in a state that the stent graft 60 is expanded in a main blood vessel V1 as illustrated in FIG. 12A, the contracted stent graft 50 is positioned e.g. such that the branching portion 35 is inserted from the inside of the stent graft 60, and then the stent graft 50 is expanded. At this time, as illustrated in FIG. 13, the stent graft 50 is indwelled such that the inner face of the branching portion 35 on the stent graft 60 is brought into contact with the outer face of the one end portion 51 on the stent graft 50. Since the annular member 70 is made of a high elasticity material silicone rubber, a radially inward force is applied from the annular member 70 to the stent graft 50, and as a result, the branching portion 35 is brought into close contact with the stent graft 50.

Figure 13:
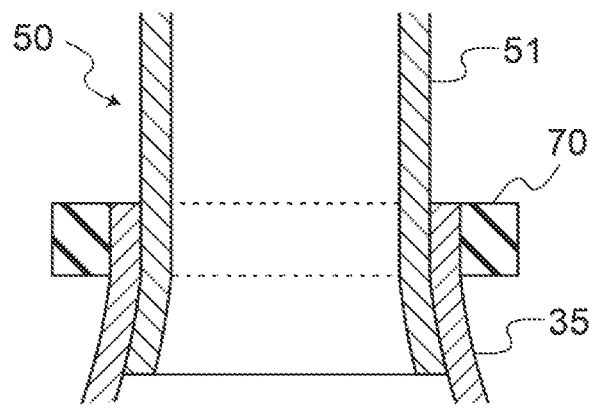
FIG. 13 is an enlarged cross-sectional drawing of the vicinity of the annular member in a state the branching blood vessel stent graft is attached to the branching portion of the stent graft.

As explained above, since the stent graft 60 according to the second embodiment includes the aforementioned annular member 70, the one end portion 51 of the stent graft 50 can be sufficiently brought into close contact with the opening edge 38 of the appropriately opening branching portion 35 (see FIG. 13). That means, since the stent graft 60 according to the second embodiment has high adhesive strength for attaching the stent graft 50 to the branching portion 35, the stent graft 60 can be appropriately indwelled in the branching part of the main blood vessel (tubular tissue). In addition, since the stent graft 60 includes the annular member 70, the through-hole 36 of the branching portion 35 sufficiently opens, and therefore insertability (ease in insertion) of the stent graft 50 into the branching portion 35 for attaching the stent graft 50 to the branching portion 35 can be improved.

In the stent graft 60 according to the second embodiment, the annular member 70 is made of a silicone rubber having relatively high elasticity (high elasticity material), and therefore the adhesiveness for attaching the stent graft 50 to the branching portion 35 can be improved.

Since the stent graft set 6 and the stent graft-indwelling device 1 according to the second embodiment include the aforementioned stent graft 60, adhesiveness for attaching the stent graft 50 to the branching portion 35 is strong.

Note that the present invention is not limited to the examples described in the aforementioned second embodiment, and can be implemented in various aspects without departing from the gist of the present invention. For example, the following modifications are also possible.

Figure 14:
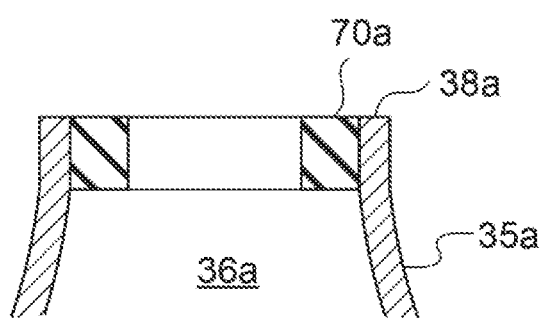
FIG. 14 is an enlarged cross-sectional drawing of the peripheral part of the branching portion, which is a first modification example of the stent graft according to the second embodiment.
Figure 15:
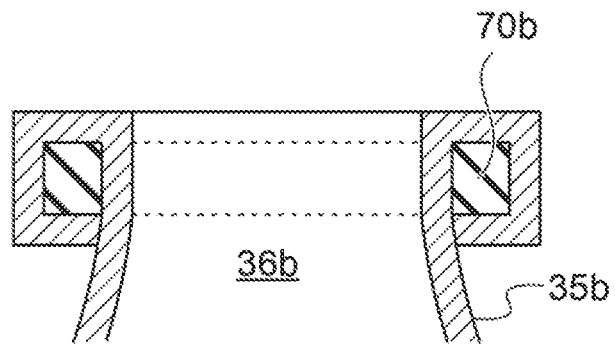
FIG. 15 is an enlarged cross-sectional drawing of the peripheral part of the branching portion, which is a second modification example of the stent graft according to the second embodiment.

In the second embodiment, although the case that the annular member 70 is situated on the outer peripheral face of the through-hole 36 on the branching portion 35 has been explained as an example, the present invention is not limited to this case. For example, as illustrated in FIG. 14, an annular member 70a may be situated on the inner peripheral face of the through-hole 36a on the branching portion 35a (in FIG. 14, inner peripheral face of an opening edge 38a). In this case, when avoiding a risk (problem of thrombus generation, or the like) possibly caused by exposure of the annular member 70a to the blood flow path, it is preferable that the branching blood vessel stent graft 50 is inserted into the branching portion 35a, and the annular member 70a is sandwiched from its both sides between the branching portion 35a and the branching blood vessel stent graft 50. In addition, as illustrated in FIG. 15, on an outer peripheral face of a through-hole 36b on a branching portion 35b, an outer surface of an annular member 70b may be surrounded by the branching portion 35b. In this case, the annular member 70b is not exposed to the blood flow path, and therefore the risk can be avoided.

Figure 16:
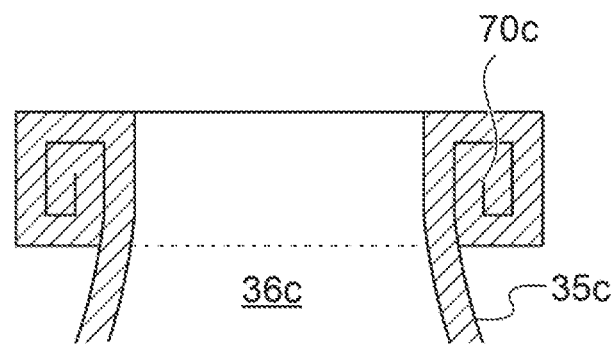
FIG. 16 is an enlarged cross-sectional drawing of the peripheral part of the branching portion, which is a third modification example of the stent graft according to the second embodiment.

In the second embodiment, although the case that the annular member 70 is situated as the opening state-maintaining portion has been explained as an example, the present invention is not limited to this case. For example, a branching portion 35c illustrated in FIG. 16 is fixed such that an end portion 70c of the branching portion 35c is folded outward in a radial direction, and is configured to maintain an opening state of a through-hole 36c when the main body portion is expanded. This folded end portion 70c is a part having a function as an opening state-maintaining portion. A method or the like for fixing a number of folds, a folding direction, folding parts on the end portion of the branching portion 35c can be appropriately changed, but it is preferable that the method can maintain the opening state of the through-hole 36c when the main body portion 31 is expanded.

Figure 17:
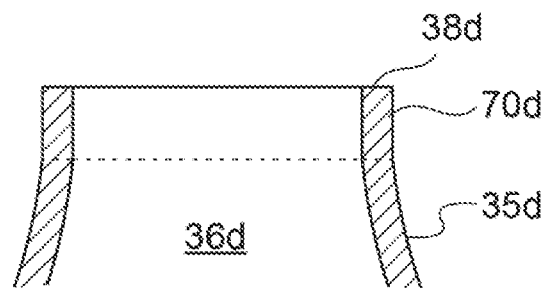
FIG. 17 is an enlarged cross-sectional drawing of the peripheral part of the branching portion, which is a fourth modification example of the stent graft according to the second embodiment.

In addition, a branching portion 35d illustrated in FIG. 17 is configured such that an opening state of a through-hole 36d is maintained when the main body portion 31 is expanded, by providing a special processing to an end portion 70d of the branching portion 35d. This specially processed end portion 70d is a part having the function as the opening state-maintaining portion. As the special processing, various methods can be adopted, e.g. a strength of the end portion 70d is enhanced by subjecting a resin material to heat treatment or the like.

Figure 18:
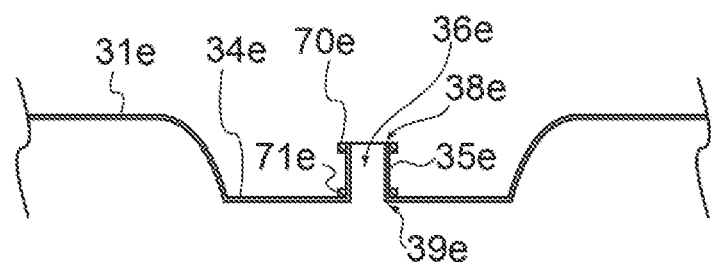
FIG. 18 is an enlarged cross-sectional drawing of the peripheral part of the branching portion, which is a fifth modification example of the stent graft according to the second embodiment.

Also, for example, as illustrated in FIG. 18, a branching portion 35e may include not only an annular member 70e situated on an opening edge 38e of the branching portion 35e, but also an annular member 71e situated on a boundary part (root part 39e) between the branching portion 35e and a concave portion 34e (tube wall of a main body portion 31e). In such a way, the annular members 70e and 71e may be situated on both the opening edge 38e and the root part 39e of the cylindrical branching portion 35e, or alternatively may be situated on either the opening edge 38e or the root part 39e of the cylindrical branching portion 35e.

In the second embodiment, although the case that the annular members 70 is made of a silicone rubber as a high elasticity material has been explained as an example, the present invention is not limited to this case. For example, the annular member 70 may be formed of a rubber material other than silicone, or a material other than rubber (e.g. a metal). In addition, the annular member 70 may be formed of a material including a rubber or the like as a main material and additionally a radiopaque substance such as barium sulfate as a submaterial. In this case, a position, an orientation, and the like of the annular member 70 can be easily grasped during contrast radiography.

In the second embodiment, although the case that the annular member 70 is a circle (ring shape) has been explained as an example, the present invention is not limited to this case. For example, the annular member 70 may be formed in a polygonal annulus, or a partially missing annular shape (e.g. U-shape, or the like). Furthermore, in the aforementioned embodiment, although the case that the cross-section of the annular member 70 is a quadrangle has been explained as an example, the present invention is not limited to this case. The annular member 70 may be formed in a polygon other than quadrangle, a circle, a raindrop shape, or a polygon of which at least some corners are rounded.

In the first and second embodiments, although the case that the branching portion 35 having the through-hole 36 (side opening) is formed in a cylindrical shape protruding outward in the radial direction of the main body portion 31 has been explained as an example, the present invention is not limited to this case. For example, it is allowable to take a configuration that the opening 37 is located on the same plane as the tube wall of the main body portion 31, and the opening state-maintaining portion is disposed on the edge of the opening 37.

In the first and second embodiments, although the stent grafts 30 and 60 including the frame portion 32 made of a thin metal wire have been explained as examples, the present invention is not limited to these stent grafts. The present invention can also be applied to a stent graft including a frame portion made of a material other than metal (e.g. ceramic, resin, or the like). Also, in the first and second embodiments, although the self-expandable stent grafts 30 and 60 have been explained as examples, the present invention is not limited to these stent grafts. The present invention can also be applied to a balloon-expandable stent-graft. Furthermore, although the case that frame portion 32 is composed of the five frame pieces 321 to 325 has been explained as an example, the present invention is not limited to this case. The frame portion 32 may be composed of not more than four frame pieces, or not less than six frame pieces.

In the first and second embodiments, although the case that the branching portion 35 (part excluding the annular member 70 in the second embodiment) is made of the same material as of the graft portion 33 of the main body portion 31 and is formed integrally with the graft portion 33 has been explained as an example, the present invention is not limited to this case. It is allowable to take a configuration that the branching portion 35 and the graft portion 33 are individually composed of independent members, and these two members are bonded to each other. In this case, the branching portion 35 may be made of a material which is the same as or different from the material of the graft portion 33.

In the first and second embodiments, although the case that the stent graft 30 or 60 includes one branching portion 35 has been explained as an example, the present invention is not limited to this case. The present invention can also be applied to a stent graft including a plurality of branching portions 35.

In the first and second embodiments, although the stent grafts 30 and 60 have been explained as examples of the tubular therapeutic implements, the present invention is not limited to the stent grafts. For example, the present invention can also be applied to another indwelling tubular therapeutic implement such as an artificial blood vessel. In addition to the thoracic aorta stent graft, examples of the stent graft include an abdominal aorta stent graft and a thoracoabdominal aorta stent graft. Furthermore, the present invention can also be applied to a tubular therapeutic implement intended to be indwelled in an organ other than blood vessel (e.g. digestive tract, bile duct, or the like).

Disclosure contents of specifications, figures, and abstracts included in Japanese Patent Application No. 2017-204028 filed on Oct. 20, 2017, and Japanese Patent Application No. 2017-206517 filed on Oct. 25, 2017 are all incorporated in this application.

REFERENCE SIGNS LIST

1 Stent graft-indwelling device (tubular therapeutic implement indwelling device)
5, 6 Stent graft set (tubular therapeutic implement set)
30, 60 Stent graft (first tubular therapeutic implement)
31, 31*e* Main body portion
32, 52 Frame portion
321, 322, 323, 324, 325 Frame piece
33, 53 Graft portion
34, 34*e* Concave portion
35, 35*a*, 35*b*, 35*c*, 35*d*, 35*e* Branching portion
36, 36*a*, 36*b*, 36*c*, 36*d*, 36*e* Through-hole (side opening)
37 Opening
38 Opening edge
40 Connecting member
70, 70*a*, 70*b*, 70*e*, 71*e* Annular member (opening state-maintaining portion)
70*c*, 70*d* End portion of branching portion (opening state-maintaining portion)
50 Branching blood vessel stent graft (second tubular therapeutic implement)
51 One end portion of stent graft 50
h1 Protrusion height of branching portion
h2 Depth of concave portion
P First region
Q Second region
V1 Main blood vessel
V2 Branching blood vessel

What is claimed is:
1. A tubular therapeutic implement comprising:
a frame portion having a plurality of frame pieces; and
a graft portion in a tubular shape disposed along the frame portion, wherein
a tube wall of the graft portion has a side opening communicating with an inner cavity of the graft portion,
the frame portion includes a first frame piece extending circumferentially while bending to form a complete ring shape and a second frame piece extending circumferentially while bending and being partially discontinuous to form a partial ring shape,
the first frame piece and the second frame piece are disposed apart in the axial direction of the graft portion,
the side opening is disposed in a specific portion of a full-length portion extending from one end to a different end through an entirety of the graft portion,
the specific portion is divided into first and second regions in a circumferential direction, the first region not having the second frame piece, the second region having the second frame piece
the first region is a region sandwiched between a first straight portion at one end of the second frame piece and a second straight portion at the other end of the second frame piece, and
the side opening is disposed in the first region.

2. The tubular therapeutic implement according to claim 1, wherein
the specific portion has a circular cross-section,
the first region is present within a range of 90° or more to 180° or less out of a full 360° circumference of the circular cross-section of the specific portion, and
the second region is present in a range excluding the first region.

3. The tubular therapeutic implement according to claim 2, wherein
the position of the side opening deviates from a middle position of the first region in the circumferential direction.

4. The tubular therapeutic implement according to claim 1, wherein
a concave portion recessed inward in a radial direction is formed on the tube wall in the graft portion,
the side opening is disposed on a cylindrical branching portion protruding outward in the radial direction by a predetermined length from the concave portion, and
the concave portion corresponds to the first region.

5. The tubular therapeutic implement according to claim 4, wherein the branching portion has an opening state-maintaining portion to maintain an opening state of the side opening when the graft portion is expanded.

6. A tubular therapeutic implement set comprising:
a first tubular therapeutic implement; and
a second tubular therapeutic implement in a tubular shape having openings on both ends, wherein
the first tubular therapeutic implement includes the tubular therapeutic implement according to claim 1, and
the second tubular therapeutic implement is configured to be attachable to the side opening of the first tubular therapeutic implement.

7. A tubular therapeutic implement indwelling device to indwell a tubular therapeutic implement expandable in a radial direction, wherein
the tubular therapeutic implement includes the tubular therapeutic implement according to claim 1.

8. The tubular therapeutic implement according to claim 1, wherein the first region is a flat surface.

9. The tubular therapeutic implement according to claim 1, wherein the first straight portion and the second straight portion are parallel.

10. The tubular therapeutic implement according to claim 4, wherein the concave portion includes a flat bottom surface corresponding to the first region,
the first straight portion and the second straight portion are disposed along the outline of the flat bottom surface.

* * * * *